(12) United States Patent
Grandmontagne et al.

(10) Patent No.: US 6,242,099 B1
(45) Date of Patent: Jun. 5, 2001

(54) MICROCAPSULES MADE OF CHITIN OR OF CHITIN DERIVATIVES CONTAINING A HYDROPHOBIC SUBSTANCE, IN PARTICULAR A SUNSCREEN, AND PROCESS FOR THE PREPARATION OF SUCH MICROCAPSULES

(75) Inventors: Bernard Grandmontagne, Plouguerneau; François Marchio, Paris, both of (FR)

(73) Assignee: Merck S.A., Nogent-sur-Marne (FR)

( * ) Notice: Subject to any disclaimer, the term of this patent is extended or adjusted under 35 U.S.C. 154(b) by 0 days.

(21) Appl. No.: 09/101,954
(22) PCT Filed: Nov. 20, 1997
(86) PCT No.: PCT/FR97/02095
§ 371 Date: Aug. 17, 1998
§ 102(e) Date: Aug. 17, 1998
(87) PCT Pub. No.: WO98/22210
PCT Pub. Date: May 28, 1998

(30) Foreign Application Priority Data

Nov. 21, 1996 (FR) .................................................. 96 14215

(51) Int. Cl.$^7$ ...................................................... B32B 5/16
(52) U.S. Cl. ................................. 428/402.2; 428/402.24; 428/403; 428/407
(58) Field of Search ................................... 428/403, 407, 428/402.2, 402.24

(56) References Cited

U.S. PATENT DOCUMENTS

| | | | |
|---|---|---|---|
| 4,016,098 | * | 4/1977 | Saeki et al. ........................... 252/316 |
| 4,687,657 | * | 8/1987 | Clark et al. ........................... 423/412 |
| 5,077,052 | * | 12/1991 | Franzoni et al. ...................... 424/438 |
| 5,521,089 | * | 5/1996 | Ishiguro et al. .................. 435/255.2 |
| 5,536,508 | * | 7/1996 | Canal et al. .......................... 424/501 |
| 5,594,694 | * | 1/1997 | Roohparvar et al. ................ 365/201 |
| 5,700,486 | * | 12/1997 | Canal et al. .......................... 424/501 |
| 5,705,270 | * | 1/1998 | Soon-Shiong et al. ........... 428/402.2 |
| 5,744,155 | * | 4/1998 | Friedman et al. .................... 424/434 |

FOREIGN PATENT DOCUMENTS 342557   11/1989   (GB).
615979   9/1994    (GB).

* cited by examiner

*Primary Examiner*—H. Thi Le
(74) *Attorney, Agent, or Firm*—Jacobson, Price, Holman & Stern, PLLC

(57) ABSTRACT

Microcapsules involving a wall of chitin or chitin derivatives or of polyhydroxylated polyamines or one of their salts, with the wall sheathing a hydrophobic substance, are prepared by forming a hydrophobic phase emulsion of the hydrophobic substance in an aqueous phase containing an anionic surfactant capable of causing insolubilization of chitosan or chitosan derivatives or polyhydroxylated polyamines, mixing the emulsion with a chitosan or chitosan derivative or polyhydroxylated polyamine organic salt so as to cause the coacervation of the chitosan or the chitosan derivatives or the polyhydroxylated polyamines around the droplets of the hydrophobic phase, subjecting the chitosan or chitosan derivative or the polyhydroxylated polyamine coacervate to an acetylation or crosslinking reaction and recovering the microcapsules, and are applicable to cosmetic compositions incorporating sunscreens.

28 Claims, 1 Drawing Sheet

MICROCAPSULES MADE OF CHITIN OR OF CHITIN DERIVATIVES CONTAINING A HYDROPHOBIC SUBSTANCE, IN PARTICULAR A SUNSCREEN, AND PROCESS FOR THE PREPARATION OF SUCH MICROCAPSULES

The present invention relates to the field of microcapsules containing a hydrophobic (or liposoluble) substance of interest.

It also relates to a process for the preparation of these microcapsules and to the application of the latter in cosmetics and pharmaceuticals, in particular.

The use of water-in-oil or oil-in-water emulsions, or of alternative forms of the latter, are advantageous solutions when it is desired to bring liposoluble active compounds into contact with the skin. This technique, which is widely used for cosmetic and pharmaceutical care purposes, reaches its limits when, for example, the molecule must not spread into the horny layers or evaporate or be removed in any other way.

The use of microcapsules or nanocapsules (hereinafter defined by the generic term "microcapsules") containing liposoluble derivatives is an advantageous alternative to emulsions, in particular when it is desired to make the contact of a molecule with the dermis lasting. Well controlled, the capsules can trap active principles, keeping them isolated or releasing them as desired.

This is because while, for certain derivatives, it is essential to keep them concentrated in order to retain the effectiveness thereof, indeed to increase it, their diffusion with time is desirable for other derivatives. The use of encapsulated molecules makes possible one or the other.

In particular, in the field of anti-sun protection, accelerated skin aging and detrimental changes due to UVA and UVB radiation have made people aware of the dangers of solar radiation and increased the need for protective creams. The main active components of these cosmetics are sunscreens which, although very efficient, are not always very well tolerated by all skin types.

In order to limit, if not overcome, this difficulty, it appears desirable to decrease the contact with the skin during the application of these products by trapping the screening agents in capsules.

Provision has for example been made, in Patent Application EP-A-0,509,904, for microcapsules containing a sunscreen obtained by complex coacervation by means of two colloidal aqueous solutions containing polymers of opposite electrical charge.

Complex coacervation is generally applied to the encapsulation of a material of lipophilic nature emulsified in an aqueous solution of polymers which are intended to form the wall of the microcapsules.

This is because it is generally known that, when two colloidal aqueous solutions respectively containing an anionic polymer and a cationic polymer are mixed in the presence of an emulsified liquid or of a suspended solid, a coacervate is formed deposited around the liquid or solid cores, to form a liquid wall isolating them from the medium. In situ curing of this liquid wall by a crosslinking agent appropriate to the nature of the polymers makes it possible to obtain stable suspended microparticles.

These microparticles are generally formed based on gelatin as cationic polymer and on polysaccharide as anionic polymer.

It is generally possible to produce, by coacervation, capsules with variable sizes in the region of 10 to 100 μm.

These systems are not completely satisfactory, due either to the type of polymers used to produce the membrane, such as collagen, gelatins, guars or gums arabic, alone or as a mixture, or due to the sizes obtained, when polysaccharides are used, for example.

This is because, in order for protection to be efficient and to no longer result in skin intolerance, the capsules must be particularly impermeable. Moreover, for the photochemical efficiency to endure, at the same concentration, the screening agents must be as fully dispersed as possible and not able to be diluted and the capsules must be as small as possible.

Moreover, the size is an essential factor in the efficiency of the screening agent. The smaller the size, the greater the protection.

It is also possible to produce solid matrix systems, of very small size, of less than a micron, from waxes which have been melted beforehand, emulsified and cooled. Nevertheless, these drastic techniques give permeable spheres which are unstable in conventional cosmetic formulations. Their short lifetime limits their interest.

Such a preparation is described, for example, in Patent Application WO-A-95/28912.

It has now been found, unexpectedly, that it is possible to prepare capsules made of chitin or of one of its derivatives, with a size of less than one mm, which meet both the requirements of impermeability and of very small size and which have an organic biocompatibility which ensures their harmlessness.

Chitin is the structural polymer of arthropods, crustaceans and insects and forms part of the membrane of certain fungi. It provides the endoskeleton of cephalopods with strength. It is in the animal world the counterpart of cellulose in the plant kingdom.

Its distinctive feature is its chemical inertia. It shows little reactivity, is insoluble in most known organic solvents and cannot, either, be thermoformed. It is only by converting it to chitosan that it becomes possible to make use of it.

It is necessary, to modulate the chitin, to proceed in two stages. The first consists in converting the chitin to chitosan and then the second in reconverting the chitosan to chitin.

A description is thus given, in Patent Application EP-A-0,013,181, page 2, of a preparation of chitin by N-acetylation of chitosan with acetic anhydride in a pyridine solution or a perchloric acid solution.

Chitin derivatives have also been prepared. Patent Application EP-A-0,013,181 describes the preparation of N-acetyl carboxyalkylchitin by acetylation of deacetylated carboxyalkylchitin with an anhydride of an organic acid. Other chitin derivatives are also mentioned, such as hydroxyalkylchitins. The material obtained can be shaped as spherical particles which can be used as ion-exchange resins.

Patent Application EP-A-0,021,750 describes a process for the preparation of chitin by acylation of deacetylated chitin in the presence of an organic acid anhydride and of a suspending agent, such as a sorbitan monoester.

Patent Application EP-A-0,026,618 describes a material comprising a mixture of two or more etherified chitin derivatives obtained by the same acetylation process indicated for the two abovementioned documents. The spherical materials obtained can in particular be used as ion-exchange resins.

However, these documents do not in any way describe microcapsules made of chitin or of chitin derivatives.

The Inventors have demonstrated, unexpectedly, that it is possible to convert, in a stable way, an alkyl sulphate or aryl sulphate or phosphate salt of chitosan or of chitosan derivatives by acetylation or by crosslinking or any other coupling method. Moreover, this stable conversion can also be applied to other polymers which react under the same conditions as the abovementioned chitosan salts, namely synthetic polyhydroxylated polyamines. Thus, the invention also applies to synthetic polyhydroxylated polyamines which couple in the presence of sulphate-containing or phosphate-containing surfactants to give, after acetylation or crosslinking, stable salts.

The present invention relates to novel microcapsules, characterized in that they are formed of a wall made of chitin or of chitin derivatives or of polyhydroxylated polyamines or a salt of the latter, the said wall enveloping a hydrophobic substance.

The present invention more particularly relates to novel microcapsules, characterized in that they are formed of a wall made of chitin or of chitin derivatives or a salt of the latter, the said wall enveloping a hydrophobic substance.

Figure 1:
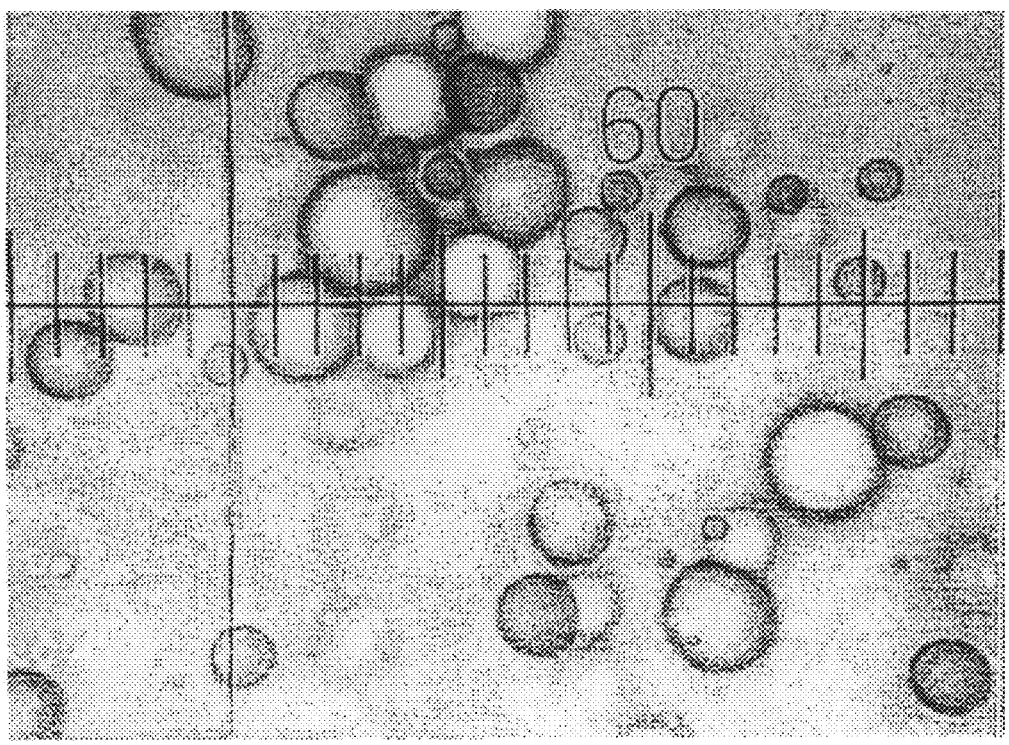
FIG. 1 is a microscope image of sunscreen microcapsules.

These microcapsules exhibit, in addition to their controlled impermeability and their biocompatibility, several other notable physical properties, among which may be mentioned:

insolubility in all organic solvents and conventional cosmetic solvents, leaktightness in cosmetic media, high dispersibility in aqueous or aqueous/alcoholic medium, a positive zeta potential, ability to be spread over the surface of the skin in a homogeneous and lasting way due to their residual cationic charge.

Microcapsule is understood to mean any particle formed of a wall enveloping a hydrophobic substance of interest.

For this reason, microcapsules are distinguished from microspheres, the polymeric material of which forms a matrix in which the said substance is embedded.

Microcapsule is understood to mean both microcapsules, strictly speaking, and nanocapsules (with a mean size of less than a micron).

Moreover, the term microparticle wall means that this wall is stable, unlike a coacervate. The term "wall" thus refers to stabilization by acetylation or crosslinking.

It should be noted that the document EP-A-615,979 describes carboxymethyl polysaccharides, in particular carboxymethylchitin, which are partially esterified. However, this document does not describe or suggest in any way chitin microcapsules. This is because it is not sufficient to record, in column 3, lines 16 and 17, that these esters may be useful in pharmaceutical formulation for the preparation of capsules or of microcapsules to enable a person skilled in the art to prepare these microcapsules, for the difficulty lies precisely in this preparation.

Likewise, the document EP-A-342,557 describes the same carboxymethylchitin esters and refers simply, column 3, lines 26 and 27, to the use of these esters in the preparation of microcapsules. This document does not describe or suggest either the preparation of these microcapsules and the microcapsules obtained.

Moreover, there exists an essential difference between carboxymethylchitin and the chitin or chitin derivatives according to the invention.

Carboxymethylchitin is of the R—O—$CH_2$—$CO_2^-$ type. It relates to soluble derivatives.

In contrast, the chitin derivatives according to the invention, which thus have properties similar to chitin, are very clearly insoluble. It will be recalled that they are principal constituents of the carapaces of crustaceans which live in water.

The invention particularly relates to the microcapsules formed of a wall of chitin.

Chitin or poly(N-acetyl-D-glucosamine) is a polysaccharide, the units of which are connected to one another via β-1,4-glycoside bridges. It is therefore distinguished from chitosan, which is an N-deacetylated chitin. When deacetylation is complete, a particular chitosan is obtained, the polyglucosamine.

Chitin is naturally deacetylated above 5% and more. The term chitosan is restricted to derivatives which, having been subjected to deacetylation, become soluble in an acidic aqueous medium. For this, a degree of deacetylation of at least greater than 65% is necessary. This level will influence the physical properties of chitosan, solubility and viscosity, but also its biochemical behaviour.

Chitin, chitosan and their oligomers and monomers are not immunogenic. They are biocompatible and very well tolerated by living tissues. The $LD_{50}$ of chitosan is 18 g per kg (value very similar to that of table sugar). These characteristics make it a product which can be very easily contaminated and it is not rare to find therein from 500,000 to 1 million germs per gram of raw material.

Techniques for the sterilization of the products are today well known. Gamma irradiation can be employed when complete sterilization is desired. If not, many preservatives make it possible to keep solutions below 1000 germs/g (cosmetic restrictions). Autoclave sterilization can be carried out on the crude products and on the gels but must be avoided on the solutions which, for their part, rapidly degrade above 40° C.

The chitin derivatives affected by the invention are in particular etherified derivatives of chitin, such as those described by the abovementioned Patent Applications EP-A-0,013,181, EP-A-0,021,750 and EP-A-0,026,618.

In particular, the O-carboxyalkyl, O-hydroxy-alkyl, O-dihydroxyalkyl or O-alkyl derivatives. Mention will also be made of the chitin derivatives comprising the N-substituted derivatives, in particular N-carboxyalkyl, N-hydroxyalkyl, N-dihydroxyalkyl or N-alkyl derivatives.

The chitin derivatives or the polyhydroxylated polyamines constituting the wall can also result from the crosslinking of chitosan or of a chitosan derivative or of the polyhydroxylated polyamines by an agent, such as glutaraldehyde or a diisocyanate.

The salts of chitin or of chitin derivatives or of the polyhydroxylated polyamines are in particular the alkali metal or alkaline earth metal, ammonium, acetic acid or hydrochloric acid salts, and the like.

The invention preferably relates to chitin microcapsules.

The microcapsules generally comprise 5 to 50% by weight of hydrophobic substance, preferably between 33 and 45%.

They advantageously exhibit a mean size of between 0.1 μm and 30 μm, preferably a mean size of between 0.3 and 10 μm.

They preferably exhibit a zeta potential of between 20 mV and 50 mV.

The hydrophobic substance can be a compound which is solid at the temperature of use of the microcapsules but, preferably, a liquid substance which can be the compound of interest itself or the compound of interest in solution in an organic solvent.

These substances are chosen in particular from compounds for cosmetic or pharmaceutical use or chromogenic agents, optionally in organic solution. The hydrophobic substance is preferably a pure sunscreen, or a sunscreen diluted in an oil, chosen from the following group:

cinnamic esters, para-aminobenzoic acid and esters, salicylic esters, benzylidenecamphor and derivatives, benzophenones, dibenzoylmethanes, benzyldiphenyl acrylates, anthranilates or triazines and more specifically: octyl methoxycinnamate, octyl dimethyl-PABA, octyl salicylate, homomenthyl salicylate, 4-methylbenzylidenecamphor, 3-benzophenone, butyl-methoxydibenzoylmethane, octocrylene, menthyl anthranilate, triazone, and the like.

The compounds are preferably chosen from the following group: 2-ethylhexyl p-methoxycinnamate, 2-ethylhexyl p-dimethylaminobenzoate, 2-ethylhexyl salicylate, 2-ethylhexyl 2-cyano-3,3-diphenylacrylate, 4-methylbenzylidenecamphor, 2-hydroxy-4-methoxybenzophenone, 4,4-butyl-4'-methoxydibenzoylmethane.

This list is not limiting and the invention applies to other sunscreens well known in the art under consideration.

The invention also relates to a composition for cosmetic or pharmaceutical use for external topical application comprising an effective amount of microcapsules according to the invention containing a substance of cosmetic or pharmaceutical interest and an inert vehicle.

In particular, the invention relates to a cosmetic or pharmaceutical composition for external topical use which absorbs UV radiation, in particular UVB and UVA radiation, comprising the microcapsules according to the invention containing a sunscreen in dispersion in an inert vehicle.

These compositions can be provided in the form of gels, creams, oils, and the like.

The invention also relates to a process for protecting the skin against UV radiation, in particular UVA or UVB radiation, characterized in that an effective amount of an abovementioned cosmetic composition is applied to the skin.

The invention also relates to a composition comprising microcapsules according to the invention containing a chromogenic agent.

The invention also relates to a process for the preparation of the microcapsules according to the invention. The process is characterized in that:

an emulsion is formed of a hydrophobic phase, composed of the hydrophobic substance, in an aqueous phase containing an anionic surface-active agent chosen from compounds capable of causing chitosan or chitosan derivatives or polyhydroxylated polyamines to become insoluble, the said emulsion is mixed with an organic salt of chitosan or of chitosan derivatives or of polyhydroxylated polyamines, so as to cause coacervation of the chitosan or of the polyhydroxylated polyamines or of the chitosan derivatives around the droplets of hydrophobic phase, the coacervate of chitosan or of polyhydroxylated polyamines or of chitosan derivatives is subjected to an acetylation or crosslinking reaction, the microcapsules are recovered.

The encapsulation process according to the invention comprises two stages. The first results in capsules with a membrane made of chitosan or of chitosan derivatives or of polyhydroxylated polyamines and then, by acetylation or crosslinking, this polymer is converted to acetylated or crosslinked chitin or chitin derivatives or polyhydroxylated polyamines, in order to increase the stability thereof.

The first stage is itself divided into two parts, which can be implemented simultaneously or otherwise. The first consists in preparing an emulsion, that is to say a suspension of lipid droplets in an aqueous phase, and the second in enveloping these droplets in a membrane made of chitosan or of chitosan derivatives or of polyhydroxylated polyamines.

To do this, a hydrophobic substance, one or more sunscreens or alternatively solutions of screening agents in a liposoluble organic medium are mixed with a surfactant in aqueous solution chosen from surfactants capable of causing coupling of chitosan or of chitosan derivatives or of polyhydroxylated polyamines. Use is advantageously made, among surfactants, of alkali metal or alkaline earth metal sulphate, phosphonate or phosphate derivatives, preferably sulphate derivatives.

The choice is advantageously made, among these derivatives, of the derivatives exhibiting a $C_6$–$C_{18}$, alkyl, $C_6$–$C_{10}$ aryl, $(C_1$–$C_{10})$alkyl$(C_6)$aryl or $(C_6)$aryl$(C_1$–$C_{10})$ alkyl residue. The choice is preferably made of a $(C_6$–$C_{18})$ alkyl sulphate in its alkaline form, in particular sodium form, and preferably still of sodium lauryl sulphate.

This surfactant is initially saturated in the mixture. Any compound which facilitates mixing or enhances the surfactant properties can be added thereto.

An improved efficiency (size of the particles) can be obtained by addition of one or more additional surfactants correctly chosen from the compounds known for this effect. Various water-soluble silicone fluids appreciably improve the process.

This mixture is subsequently added, with vigorous stirring, to a solution of chitosan or of chitosan derivatives or of polyhydroxylated polyamines prepared beforehand or simultaneously.

The chitosan or the chitosan derivatives or the polyhydroxylated polyamines couple to the surface of the lipid vesicles as a sulphate salt of chitosan or of chitosan derivatives or of polyhydroxylated polyamines which are insoluble. Each new stirring movement causes irreversible splitting of a micelle into two new vesicles. The size of the vesicles rapidly decreases and the addition of surfactants enhances the mechanism.

This technique results, after stirring for a few minutes, in an aqueous solution being obtained which contains capsules with a size in the region, by a power of ten, of a micron, characterized by a membrane composed of a surfactant (in particular alkyl sulphate) salt of chitosan or of chitosan derivatives or of polyhydroxylated polyamines.

In water, the solvation of salified chitosans or chitosan derivatives or polyhydroxylated polyamines is provided for at a pH of less than approximately 6.5. The salt used is generally an acetate but other organic ions can also be used, in particular those resulting from the dissociation of weak organic monoacids of alkyl- or aryl- or hydroxyalkylcarboxylic and acid derivative type, such as lactic, glutamic, gluconic, glycolic, benzoic, aminobenzoic, and the like, or ions with a saline equilibrium with chitosan which can be displaced by an acetylation reaction (which rules out strong acids of hydrochloric, sulphuric, phosphoric and nitric type).

The chitosan derivatives which can be used are in particular O- or N-carboxyalkylchitosan but can also be O- or N-hydroxyalkylchitosans or O- or N-alkylchitosans.

Chitosan is a polymer which is soluble in an acidic aqueous medium. Chitin is a particularly impermeable insoluble polymer. In order to render the entrapment of the oils in the capsules irreversible and to limit their destruction therein or their change therein by displacement of acid/basic salts, the membrane is reinforced by converting the chitosan by acetylation or crosslinking.

The acetylation reaction is provided by an organic acid anhydride, in particular an aliphatic organic acid [lacuna] containing 4 to 40 carbon atoms or an aromatic organic acid anhydride containing 12 to 20 carbon atoms, such as acetic anhydride, propionic anhydride, butyric anhydride, valeric anhydride or benzoic anhydride.

These anhydrides are dissolved in a polar solvent which makes possible the acetylation reaction, in particular ethyl alcohol, tetrahydrofuran, dioxane, and the like.

The acetylation reaction is well known per se.

The addition of anhydride displaces the acid/basic ionic equilibrium uniting the surfactant and the amine of the chitosan or of one of its derivatives or of the polyhydroxylated polyamines and makes it possible to thus carry out the acetylation.

Other alternative forms consist in crosslinking the coacervate of chitosan or of chitosan derivatives or of polyhydroxylated polyamines by interfacial cross-linking linking by means of glutaraldehyde or of diisocyanates. This reaction is well known in microencapsulation.

The irreversibility of the process can also be obtained by the use of polyanion/polycation interactions via the action of an anionic polymer, such as a carbopol or an alginate, or alternatively of a sulphate-containing polymer, such as a carrageenan or a fucoidan.

According to a preferred alternative form of the process taken in combination with the above, the amounts by weight of the various reactants used are as follows:

| | | |
|---|---|---|
| hydrophobic substance | 5% to 50%, | preferably 33 to 45% |
| surfactants | 0.1% to 1.5%, | preferably about 0.33% |
| salt of chitosan or of chitosan derivatives or of polyhydroxylated polyamines | 0.1% to 10%, | preferably about 2% |
| anhydride or | 0.1% to 10%, | preferably about 0.33% |
| crosslinking agent | 0.1% to 10%, | preferably about 0.33% |

The process is also notable in that it can be carried out at room temperature without supplying energy.

The invention will now be described with respect to the examples presented hereinbelow intended to illustrate the invention.

The general preparation process described in the following examples consists in mixing two phases with stirring. The size of the particles obtained is dependent on the stirring speeds and thus on the equipment employed. By way of example, stirring carried out with a simple shaft equipped with a perpendicular paddle and rotating at 8000 rev/min makes it possible to obtain capsules with a size of less than 10 $\mu$m. If stirring is carried out with a turbine mixer at 24,000 rev/min, the mean size of the capsules is then markedly lower, at 1 $\mu$m.

EXAMPLES

Example 1

40 g of 2-ethylhexyl p-methoxycinnamate sunscreen (Eusolex® 2292) are saturated with 0.4 g of sodium lauryl sulphate and 0.4 g of fluid 190 (silicone). The whole mixture is vigorously stirred at room temperature and mixed with 80 g of an aqueous solution containing 2% of chitosan salt (acetate). Stirring is maintained until vesicles with a size of less than 10 mm are obtained. An acetylating alcoholic solution of acetic anhydride is added to this micellar dispersion. The whole mixture is subsequently washed by any appropriate method necessary for the removal of the excess products.

The characteristics of the microcapsules are evaluated using four measurements:

Zeta Potential

Equipment: Malvern instrument
Cell type: Zemo 10 Ref.
Beam Mode F(Ka)=1.5 (Smoluchowsky)
Cell voltage=143.0 V
Temperature=25.4° C.
m=0.682 cp2 pH=6.59
Cell conductivity: 0.09 mS dielectric constant: 79.0
Cell position: 17.00%

Results: Zeta Potential = +32.61 mV
Mean electrophoretic mobility = 6.659 microns.cm/V.s.

Physical Strength of the Particles Methods: Treatment of the Sample with Microwave Radiation Conditions: until the suspension boils
Results: No phase separation of the suspension No rupturing of the capsules recorded by optical microscopy (magnification 400) Particle size stability (app. 1 mm).

Resistance to Extraction
Encapsulated screening agent:

Octyl methoxycinnamate (OMC), Eusolex® 2292.
Conditions: Dilutest type (suspended in various solutions, containing surfactants, and emulsions).
Filtration through 0.2 $\mu$m Anotop® filters
Sampling of the filtrate/Dilution solvent Water/Ethanol: 20:80
Measurement: UV absorption spectrophotometry; Perkin-Elmer model

| EXTRACTION SOLVENTS | % OF SCREENING AGENT RELEASED | DEGREE OF ENCAPSU-LATION |
|---|---|---|
| Water | non-detectable | 100 |
| O/W emulsion* | non-detectable | 100 |
| Aqueous solution containing 5% of Simulsol 59 | 5 | 95 |
| Aqueous solution containing 5% of Incroquat Behenyl TMS | non-detectable | 100 |

*O/W emulsion containing 18% of encapsulated screening agent: cf. measurement of the in vitro protection factor.

Particle Size Analysis

Equipment: Malvern instrument
Range: 30 HD
Beam length: 2.4 mm

Obscuration: 9.3%
Dispersant R.I.-1.3300

| Results: |
|---|
| Type of distribution: volume |
| Relative density = 3.260 g/cub.cm |
| concentration = 0.0023% |

The various diameters shown hereinbelow exhaustively express the general particle size profile from the spectrum recorded.

D(v, 0.5) mean diameter measured at 50% of the cumulative volume curve,

D(v, 0.1) mean diameter measured at 10% of the cumulative volume curve,

D(v, 0.9) mean diameter measured at 90% of the cumulative volume curve

D(3,4) diameter at which the greatest volume of particles appears (culminating point of the Gauss curve), D(3,2) mean diameter of the particles expressed by population.

| | |
|---|---|
| D(v, 0.5) | =2.00 μm |
| D(v, 0.1) | =0.63 μm |
| D(v, 0.9) | =5.39 μm |
| D(3,4) | =2.62 μm |
| D(3,2) | =1.32 μm |

Measurement of the in vitro Protection Factor of Emulsions Containing Encapsulated and Non-encapsulated 2-ethyl [hexyl] p-methoxycinnamate (OMC)

The oil-in-water emulsion has the following composition in percentage by weight:

| | |
|---|---|
| Glyceryl stearate/PEG-100 stearate | 6 |
| Isohexadecane | 6 |
| PPG-15 stearyl ether | 3 |
| Stearic acid | 4 |
| Squalane | 2 |
| Phenyl trimethicone | 0.5 |
| Dimethicone | 0.5 |
| PEG-8/tocopherol/ascorbic acid/citric acid | 0.01 |
| Propylene glycol | 2 |
| Phenoxyethanol/paba esters | 0.8 |
| Demineralized water | q.s. for 100 | to which the encapsulated or non-encapsulated OMC is added.

The various diameters exhaustively express the general particle size profile from the spectrum recorded. Thus, the main value D(v, 0.5) corresponds to the mean diameter of the particles, measured at 50% of the cumulative volume curve. In other words, at the value shown, 50% of the volume of the particles is below this value and 50% above.

D(v, 0.1)=mean diameter of the population of the smallest particles, measured at 10% of the cumulative volume, and the like.

D(3,4) expresses the diameter at which the greatest volume of particles appears (culminating point of the Gauss curve).

Finally, D(3,2) corresponding to the mean diameter of the particles expressed as population and no longer as volume. This value is not directly expressed by the measurements but is calculated from a mathematical formula. As the volume of a big particle is much larger than that of a small particle, it is advisable also to take into account the number in order to complete the statistical profile of the sample analysed.

Diffey Method

Equipment and Method

The antisun preparation is applied to a substrate of Transpore® (3M Co.) tape type with an indented surface similar to the topography of the stratum corneum.

The principle amounts to measuring the spectral transmission of U.V. radiation through this Transpore® tape with and without the antisun preparation.

The U.V. radiation source (Xenon Lamp) emits a luminescent spectrum with a continuous distribution between 290 and 400 nm. The luminescent emission passes through the 10 mm quartz lens of a spectroradiometer (Optronic model 742, Optronic Labs. Inc.) connected to a computer. The wavelengths are calibrated by means of a low-pressure mercury vapour lamp (253.7 nm and 435.8 nm).

The application doses of the test preparation are 2 mg/cm of substrate.

The monochromatic protection factor at a wavelength is given from the "signal recorded through the virgin tape to the signal measured in the presence of the test product". For each product, the transmission is determined on 3 different tapes and a mean protection factor $[PF(\lambda)]$ is calculated with the standard deviation $[\Delta P (\lambda)]$.

The sun protection factor is evaluated from the transmission measurements according to the formula:

$$SPF = \sum_{290}^{400} E(\lambda) \bigg/ \sum_{290}^{400} E(\lambda) \times \varepsilon(\lambda) / PF(\lambda)$$

where $E(\lambda)$ is the irradiance of sunlight at the earth's surface under defined conditions and $\varepsilon(\lambda)$ is the relative effectiveness of the UVR at the wavelength $\lambda$ inducing actinic erythema according to the reference spectrum adopted by the I.C.R.

| | Results: | |
|---|---|---|
| Active material level | Encapsulated OMC | Pure OMC |
| 6% | 6.92 | 6.74 |
| 10% | 12.05 | 11.05 |

Example 2

40 g of sunscreen according to Example 1 are saturated with 0.4 g of sodium lauryl sulphate. The whole mixture is vigorously stirred at room temperature and mixed with 80 g of an aqueous solution containing 2% of chitosan salt. Stirring is maintained until vesicles of the desired sizes are obtained. An acetylating alcoholic solution of phthalic anhydride is added to this micellar dispersion. The whole mixture is subsequently washed by any appropriate method necessary for the removal of the excess products.

Example 3

40 g of sunscreen according to Example 1 are saturated with 0.4 g of sodium lauryl sulphate. The whole mixture is vigorously stirred at room temperature and mixed with 80 g of an aqueous solution containing 2% of chitosan salt. Stirring is maintained until vesicles of the desired sizes are obtained. An acetylating alcoholic solution of propionic anhydride is added to this micellar dispersion. The whole mixture is subsequently washed by any appropriate method necessary for the removal of the excess products.

Example 4

40 g of sunscreen according to Example 1 are saturated with 0.4 g of sodium lauryl sulphate. The whole mixture is vigorously stirred at room temperature and mixed with 80 g of an aqueous solution containing 2% of chitosan salt. Stirring is maintained until vesicles of the desired sizes are obtained. An aqueous solution containing 0.1 g of glutaraldehyde is added to this micellar dispersion. The whole mixture is subsequently washed by any appropriate method necessary for the removal of the excess products. The membrane of the capsule is subsequently neutralized with a solution containing 0.1 to 0.5 g of para-aminobenzoic acid.

Example 5

40 g of sunscreen according to Example 1 are saturated with 0.4 g of sodium lauryl sulphate. The whole mixture is vigorously stirred at room temperature and mixed with 80 g of an aqueous solution containing 2% of chitosan salt. Stirring is maintained until vesicles of the desired sizes are obtained. A 0.5% sodium alginate solution is added to this micellar dispersion with stirring, in order to create a polyanion-polycation coupling complex. The whole mixture is subsequently washed by any appropriate method necessary for the removal of the excess products.

Example 6

40 g of 2-ethylhexyl p-dimethylaminobenzoate (Eusolex 6007®) sunscreen are saturated with 0.4 g of sodium lauryl sulphate and 0.4 g of fluid 190 (silicone). The whole mixture is vigorously stirred at room temperature and mixed with 80 g of an aqueous solution containing 2% of chitosan salt. Stirring is maintained until vesicles with sizes of less than 10 m are obtained. An acetylating alcoholic solution of acetic anhydride is added to this micellar dispersion. The whole mixture is subsequently washed by any appropriate method necessary for the removal of the excess products.

Example 7

40 g of the above sunscreen are saturated with 0.4 g of sodium lauryl sulphate. The whole mixture is vigorously stirred at room temperature and mixed with 80 g of an aqueous solution containing 2% of chitosan salt. Stirring is maintained until vesicles of the desired sizes are obtained. An acetylating alcoholic solution of phthalic anhydride is added to this micellar dispersion. The whole mixture is subsequently washed by any appropriate method necessary for the removal of the excess products.

Example 8

40 g of the above sunscreen are saturated with 0.4 g of sodium lauryl sulphate. The whole mixture is vigorously stirred at room temperature and mixed with 80 g of an aqueous solution containing 2% of chitosan salt. Stirring is maintained until vesicles of the desired sizes are obtained. An aqueous solution containing 0.1 g of glutaraldehyde is added to this micellar dispersion. The whole mixture is subsequently washed by any appropriate method necessary for the removal of the excess products. The membrane of the capsule is subsequently neutralized with a solution containing 0.1 to 0.5 g of para-aminobenzoic acid.

Examples 9 to 13

2-Ethylhexyl p-methoxycinnamate is replaced in Examples 1 to 5 by a mixture of 2-ethyl p-methoxycinnamate and 2-ethylhexyl p-dimethylaminobenzoate.

In the various examples described, the capsules obtained predominantly have sizes of the order of a micron; their membrane is remarkably stable to the physical constraints of temperature and to aging. The alkyl sulphate residue carried on the polymer chain of the chitin and the cationic charge (20 mV<Zeta potential<50 mV) provide them with satisfactory bacteriological stability.

The appended single FIG. 1 is a microscope image of sunscreen microcapsules according to the invention with a distance between two vertical lines of 0.2 mm.

What is claimed is:

1. Microcapsules, comprising a wall of chitin or chitin derivative or polyhydroxylated polyamine or a salt of chitin or chitin derivative or polyhydroxylated polyamine, said wall enveloping a hydrophobic substance.

2. Microcapsules according to claim 1, wherein the chitin derivative is an O-carboxyalkyl, O-hydroxyalkyl, or alkyl etherified derivative or an N-carboxyalkyl, N-hydroxyalkyl, or N-alkyl N-substituted derivative of chitin.

3. Microcapsules according to claim 1, wherein the wall of a chitin derivative or polyhydroxylated polyamine results from the crosslinking of chitosan or of an O-carboxyalkyl, O-hydroxyalkyl, or alkyl etherified chitosan derivative or of an N-carboxyalkyl, N-hydroxyalkyl, or N-alkyl N-substituted chitosan derivative or from crosslinking or acetylation of a polyhydroxylated polyamine.

4. Microcapsules according to claim 1, wherein the salt of chitin or chitin derivative or polyhydroxylated polyamine is an alkali metal, alkaline earth metal, ammonium, acetic acid, or hydrochloric acid salt.

5. Microcapsules according to claim 1, wherein the hydrophobic substance is a cosmetic or pharmaceutical substance or a chromogenic agent.

6. Microcapsules according to claim 5, wherein the hydrophobic substance is a hydrophobic sunscreen.

7. Microcapsules according to claim 6, wherein the sunscreen is selected from the group consisting of:

cinnamic esters, para-aminobenzoic acid and esters, salicylic esters, benzylidenecamphor and derivatives, benzophenones, dibenzoylmethanes, benzyldiphenyl acrylates, anthranilates and triazines.

8. Microcapsules according to claim 7, wherein the sunscreen is selected from the group consisting of:

2-ethylhexyl p-methoxycinnamate, 2-ethylhexyl p-dimethyaminobenzoate, 2-ethylhexyl salicylate, 2-ethyl-hexyl 2-cyano-3,3-diphenylacrylate, 4-methylbenzylidene-camphor, 2-hydroxy-4-methoxybenzophenone, and 4,4-butyl-4'-methoxydibenzoylmethane.

9. Microcapsules according to claim 7, wherein the hydrophobic sunscreen is octyl methoxycinnamate, octyl dimethyl-PABA, octyl salicylate, homomenthyl salicylate, 4-methylbenzylidenecamphor, 3-benzophenone, butylmethoxydibenzoylmethane, octocrylene, menthyl anthranilate or triazone.

10. Composition for cosmetic or pharmaceutical use for external topical use which absorbs UV radiation, comprising microcapsules according to claim 6 and an inert vehicle.

11. Composition for cosmetic or pharmaceutical use for external topical use comprising microcapsules according to claim 5 and an inert vehicle.

12. Composition according to claim 11, in the form of a gel, a cream, or an oil.

13. Composition for pharmaceutical use comprising microcapsules containing a pharmaceutical substance according to claim 5 and an inert vehicle.

14. Microcapsules according to claim 5, wherein the hydrophobic substance is in an organic solution.

15. Microcapsules according to claim 1, comprising from 5 to 50% by weight of said hydrophobic substance.

16. Microcapsules according to claim 1, exhibiting a mean size of between 0.1 μm and 30 μm.

17. Microcapsules according to claim 16, exhibiting a mean size of between 0.3 μm and 10 μm.

18. Process for the preparation of microcapsules according to claim 1, comprising the steps wherein:

an emulsion is formed of droplets of a hydrophobic phase, composed of the hydrophobic substance, in an aqueous phase containing an anionic surface-active agent chosen from surfactants capable of causing chitosan or chitosan derivatives or polyhydroxylated polyamines to become insoluble, said emulsion is mixed with an organic salt of chitosan or of chitosan derivatives or of polyhydroxylated polyamines, so as to cause coacervation of the chitosan or of the chitosan derivatives or of the polyhydroxylated polyamines around the droplets of hydrophobic phase, the coacervate of chitosan or of chitosan derivatives or of polyhydroxylated polyamines is subjected to an acetylation of crosslinking reaction, the microcapsules are recovered.

19. Preparation process according to claim 18, wherein the anionic surface-active agent is $C_6$–$C_{18}$ alkyl, $C_6$–$C_{10}$ aryl, $(C_6$–$C_{10})$alkyl$(C_6)$aryl, or $(C_6)$aryl$(C_1$–$C_{10})$alkyl sulphate or phosphate or phosphonate, the counterion of which is an alkali metal or alkaline earth metal.

20. Preparation process according to claim 19, wherein the surfactant is an alkaline $C_6$–$C_{18}$ alkyl sulphate.

21. The preparation process according to claim 20, wherein the surfactant is sodium lauryl sulfate.

22. Preparation process according to claim 18, wherein the aqueous phase contains a water-soluble silicone fluid.

23. Preparation process according to claim 18, wherein the acetylation reaction is carried out by a solution, in a polar organic solvent, of an aliphatic organic acid anhydride containing 4 to 40 carbon atoms or an aromatic organic acid anhydride containing 12 to 20 carbon atoms.

24. Preparation process according to claim 23, wherein the anhydride is chosen from the group consisting of acetic anhydride, propionic anhydride, butyric anhydride, valeric anhydride, and benzoic anhydride.

25. Preparation process according to claim 23, wherein the amounts by weight of the various reactants are as follows:

| | |
|---|---|
| hydrophobic substance | 5% to 50%, |
| surfactants | 0.1 % to 1.5%, |
| salt of chitosan or of chitosan derivatives or of polyhydroxylated polyamines | 0.1 % to 10%, |
| anhydride or crosslinking agent | 0.1% to 10%, 0.1% to 10%. |

26. The preparation process of claim 25, wherein the amounts by weight are:

| | |
|---|---|
| hydrophobic substance | 33 to 45%, |
| surfactants | about 0.33%, |
| salt of chitosan or of chitosan derivatives or of polyhydroxylated polyamines | about 2%, |
| anhydride or crosslinking agent | about 0.33%, about 0.33%. |

27. Preparation process according to claim 18, wherein the crosslinking is carried out by means of glutaraldehyde or a diisocyanate.

28. Preparation process according to claim 18, wherein the chitosan salt is chitosan acetate.

* * * * *